United States Patent
Ishitsu et al.

(10) Patent No.: US 7,312,438 B2
(45) Date of Patent: Dec. 25, 2007

(54) RADIOLOGICAL IMAGING APPARATUS AND TIMING CORRECTION METHOD THEREFOR

(75) Inventors: Takafumi Ishitsu, Hitachi (JP); Kensuke Amemiya, Hitachinaka (JP); Yuuichirou Ueno, Hitachi (JP); Takashi Matsumoto, Hamura (JP); Takashi Matsumoto, Hadano (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/503,170

(22) Filed: Aug. 14, 2006

(65) Prior Publication Data

US 2006/0273250 A1 Dec. 7, 2006

Related U.S. Application Data

(63) Continuation of application No. 11/174,589, filed on Jul. 6, 2005, now Pat. No. 7,129,476.

(30) Foreign Application Priority Data

Sep. 24, 2004 (JP) .............................. 2004-276351

(51) Int. Cl.
*G12B 13/00* (2006.01)

(52) U.S. Cl. ................................................ 250/252.1

(58) Field of Classification Search .............. 250/252.1
See application file for complete search history.

(56) References Cited

U.S. PATENT DOCUMENTS

| 5,952,662 A * | 9/1999 | McDaniel .................... 250/369 |
| 6,080,984 A * | 6/2000 | Friesenhahn .............. 250/252.1 |
| 6,852,978 B2 * | 2/2005 | Williams et al. ........ 250/363.03 |
| 7,026,622 B2 * | 4/2006 | Kojima et al. .......... 250/363.03 |
| 2003/0128801 A1 * | 7/2003 | Eisenberg et al. ............. 378/19 |
| 2005/0067572 A1 * | 3/2005 | Amemiya et al. ...... 250/363.05 |

FOREIGN PATENT DOCUMENTS

| JP | 61-132888 | 6/1986 |
| JP | 02-017488 | 1/1990 |
| JP | 02-082439 | 3/1990 |
| JP | 6-19436 | 3/1994 |
| JP | 3343122 | 8/2002 |
| WO | WO 94/11761 | 5/1994 |

* cited by examiner

*Primary Examiner*—David Porta
*Assistant Examiner*—Christopher G Webb
(74) *Attorney, Agent, or Firm*—Dickstein Shapiro LLP

(57) ABSTRACT

A processing circuit, which carries out coincidence counting, acquires calibration data so that time delays of γ-ray detection signals from radiation detectors coincide with one another. A technique for acquiring calibration data faster and easily is provided to attain high time precision and respond to multi-channeling of detectors. A signal from a test signal generator is sent to signal processing apparatuses and coincidence count events are generated as a test. The events generated are processed by a delay time control apparatus and a variable delay circuit is controlled to improve the accuracy of coincidence counting.

19 Claims, 5 Drawing Sheets

RADIOLOGICAL IMAGING APPARATUS AND TIMING CORRECTION METHOD THEREFOR

CROSS REFERENCE TO RELATED APPLICATIONS

The application is a continuation of U.S. patent application Ser. No. 11/174,589, filed on Jul. 6, 2005 now U.S. Pat. No. 7,129,476, the disclosure of which is incorporated herein by reference in its entirety.

BACKGROUND OF THE INVENTION

The present invention relates to a radiological imaging apparatus and a timing correction method therefor, and more particularly, to a radiological imaging apparatus and a timing correction method therefor suitable for use in a Positron Emission Tomography (hereinafter referred to as "PET") apparatus.

A PET inspection is an inspection carried out by administering radio pharmaceuticals (hereinafter referred to as "PET pharmaceuticals") containing positron emitters ($^{15}O$, $^{13}N$, $^{11}C$, $^{18}F$, etc.) and having the nature of accumulating in a specific region (e.g., cancer cells) to an examinee and detecting γ-rays emitted from the affected area of the examinee by being provoked by the PET pharmaceuticals accumulated in the region using radiation detectors. When a positron emitted from the positron emitter contained in the PET pharmaceuticals encounters with neighboring electrons and annihilates, a pair of γ-rays having energy of 511 keV are emitted in substantially diametrically opposite directions. It is possible to identify locations where the PET pharmaceuticals are accumulated, that is, the affected area of cancer of the examinee based on the respective detection signals outputted from a pair of radiation detectors which have detected this pair of γ-rays.

To identify the affected area of cancer, it is necessary to identify the respective positions of the pairs of radiation detectors which have detected the pairs of γ-rays generated by annihilation of positrons and it is necessary to take a coincidence count of detection signals outputted from these radiation detectors. This requires time resolution with high precision. However, even when γ-rays enter two radiation detectors simultaneously, there is a variation in signal transmission from the respective radiation detectors to a coincidence circuit and there are differences in the times at which signals arrive at the coincidence circuit. For this reason, it is necessary to adjust transmission delays of signals from the respective radiation detectors so that the times at which signals arrive at the coincidence circuit coincide with one another.

Conventionally, timing correction of signals detected by radiation detectors is realized by acquiring calibration data using a calibration radiation source and adjusting a time variation of signal transmission based on the calibration data. This timing correction method is described, for example, in JP-B-6-19436 and Japanese Patent No. 3343122.

The signal timing correction method described in JP-B-6-19436 will be explained. First, γ-rays from the radiation source are detected by a radiation detector, a timing signal is created based on an output signal of the radiation detector and this timing signal is inputted to the coincidence count apparatus through a delay adjusting circuit. The sensitivity of the signal outputted from the coincidence count apparatus is measured. Next, the sensitivity of γ-rays from the radiation detector is measured using the same method as that described above while changing an amount of delay to be set in the delay time adjusting circuit. This is the method of correcting a signal delay time by setting the amount of delay corresponding to the highest measured sensitivity in the delay time control apparatus.

Next, the signal timing correction method described in Japanese Patent No. 3343122 will be explained. This method corrects timings of signal transmission by setting a calibration radiation source within a field of view of the PET apparatus, creating timing data indicating a time difference measured value of a coincidence event which occurs between a pair of radiation detectors, calculating a time delay value corresponding to each radiation detector and setting this time delay value in the corresponding radiation detector channel.

However, the above described conventional technologies obtain calibration data necessary for timing correction using a radiation source and γ-rays emitted for one event form a pair, and therefore it is possible to obtain calibration data for only the circuits connected to the two radiation detectors into which the respective γ-rays are introduced. For this reason, it takes a long time to obtain calibration data corresponding to all radiation detectors.

It is an object of the present invention to provide a radiological imaging apparatus and a timing correction method therefor capable of reducing a time required to acquire timing calibration data to be used for timing correction of output signals of radiation detectors.

SUMMARY OF THE INVENTION

A feature of the present invention to attain the above described object is to input a test signal outputted from a test signal generator to a plurality of signal processing apparatuses and generate timing calibration data based on the outputs of the plurality of signal processing apparatuses. Since the present invention can input a test signal to the respective signal processing apparatuses reliably, the time required to acquire timing calibration data necessary for timing correction of output signals of the radiation detectors can be reduced.

It is preferable to carry out timing correction of γ-ray detection signals from the radiation detectors based on the calibration data during an inspection of an examinee.

According to the present invention, the time required to acquire timing calibration data necessary for timing correction of output signals of the radiation detectors is shortened.

Other objects, features and advantages of the invention will become apparent from the following description of the embodiments of the invention taken in conjunction with the accompanying drawings.

DETAILED DESCRIPTION OF THE EMBODIMENTS

With reference now to the attached drawings, embodiments will be explained below.

Embodiment 1

A radiological imaging apparatus that is a preferred embodiment of the present invention will be explained below using FIG. 1 and FIG. 2. The radiological imaging apparatus of this embodiment is a PET apparatus.

Figure 1:
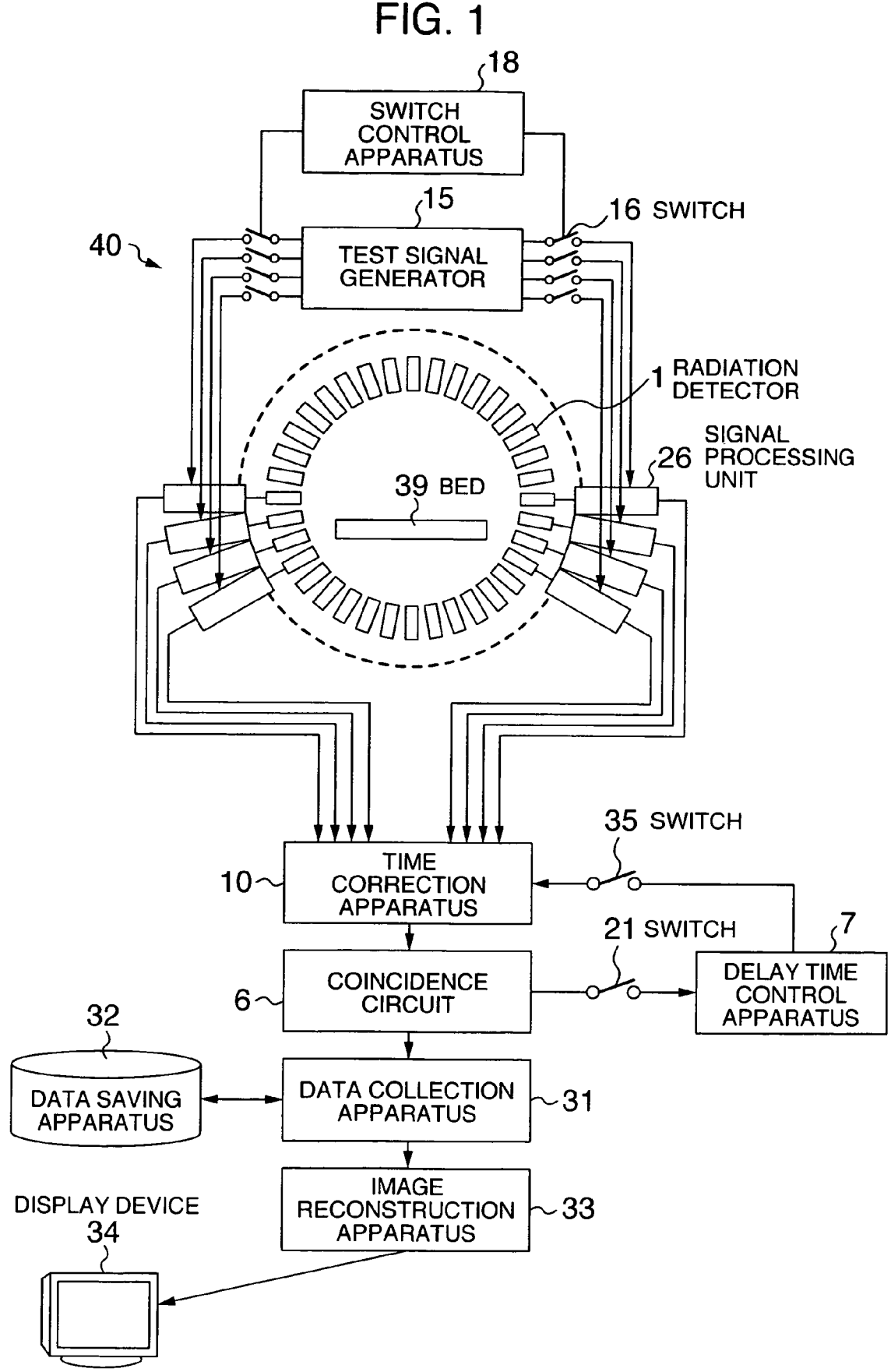
FIG. 1 is a block diagram of a PET apparatus which is an embodiment of the present invention.
Figure 2:
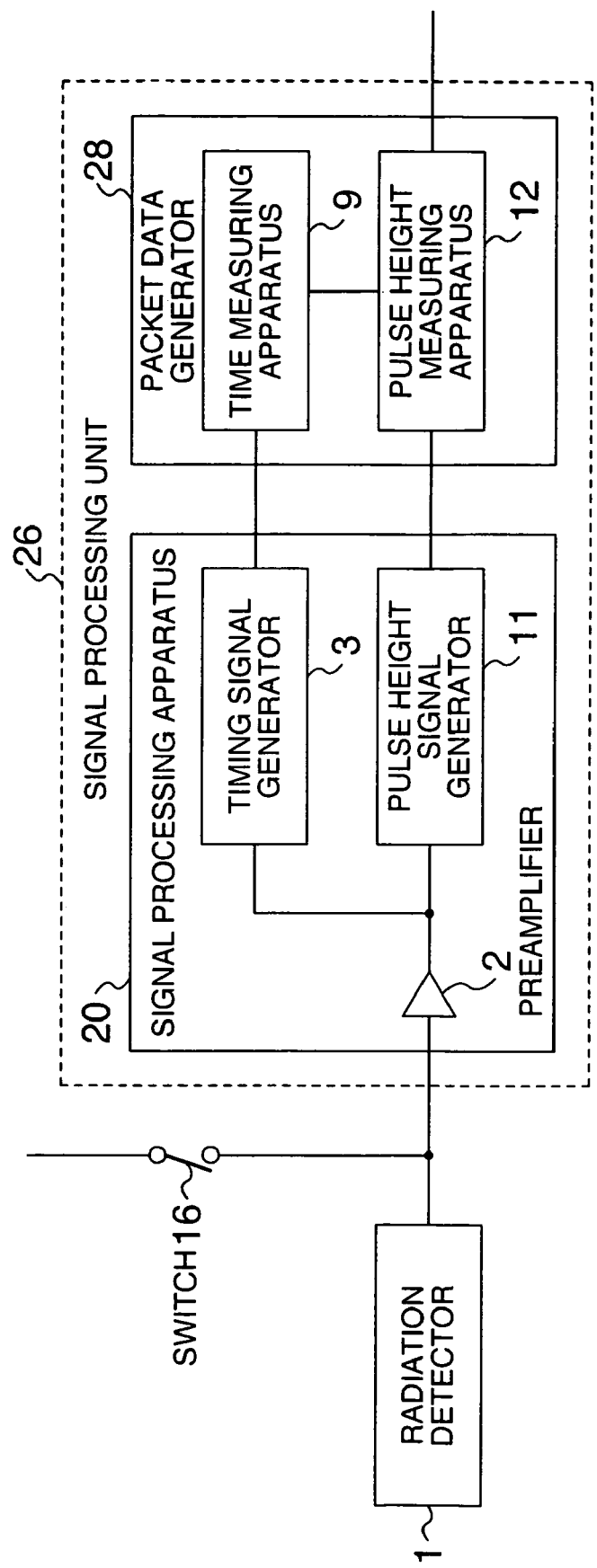
FIG. 2 is a detailed block diagram of the signal processing unit shown in FIG. 1.

As shown in FIG. 1, the PET apparatus 40 of this embodiment is provided with a bed 39 for holding an examinee (test subject), a plurality of radiation detectors 1, a plurality of signal processing units 26, a time correction apparatus 10, a coincidence circuit 6, a delay time control apparatus 7 and a test signal generator 15. The plurality of radiation detectors 1 are arranged around the bed 39 in a ring shape surrounding the bed 39. The radiation detectors 1 are also arranged in a plurality of rows in the longitudinal direction of the bed 39. The radiation detector 1 is a semiconductor radiation detector and approximately 100,000 radiation detectors 1 are provided for the PET apparatus 40. The signal processing unit 26 which is provided for each radiation detector 1 is provided with a signal processing apparatus 20 in the front stage and a packet data generator 28 in the posterior stage as shown in FIG. 2. The signal processing apparatus 20 is provided with a preamplifier 2, and a timing signal generator 3 and a pulse height signal generator 11 connected to the preamplifier 2. The preamplifier 2 is connected to the radiation detector 1. A switch (opening/closing device) 16 is connected to the signal processing apparatus 20, that is, the preamplifier 2. The switch 16 is provided for each signal processing apparatus 20. All the switches 16 are connected to the test signal generator 15. The packet data generator 28 is provided with a time measuring apparatus 9 and a pulse height measuring apparatus 12. The time measuring apparatus 9 is connected to the timing signal generator 3. The pulse height measuring apparatus 12 is connected to the pulse height signal generator 11 on one hand and connected to the time measuring apparatus 9 on the other. The time measuring apparatus 9 is connected to the time correction apparatus 10. The coincidence circuit 6 is connected to the time correction apparatus 10. The delay time control apparatus 7 is connected to the coincidence circuit 6 through a switch 21 and also connected to the time correction apparatus 10 through a switch 35. A data collection apparatus 31 connected to the coincidence circuit 6 is connected to an image reconstruction apparatus 33. A data saving apparatus 32 is connected to the data collection apparatus 31. A display device 34 is connected to the image reconstruction apparatus 33. In this embodiment, the delay time control apparatus 7 is the calibration data generator which generates calibration data.

For example, before starting a PET inspection everyday, it is possible to acquire calibration data necessary for timing correction of the PET apparatus 40 using a test signal outputted from the test signal generator 15. The test signal is an electric signal, and more specifically, a charge signal. It is difficult to send a charge signal from the test signal generator 15 to the preamplifier 2 and it is desirable to convert a voltage signal to a charge signal through the switch 16 or the preamplifier 2 using a capacitor. It is desirable to realize equi-length or equi-electric length wiring from the test signal generator 15 to the preamplifier 2, but it is also possible to obtain an amount of delay from the test signal generator 15 to the preamplifier 2 through a calculation or comparison with measurement of the delay time using a radiation source to perform correction when creating calibration data. The method of acquiring calibration data in this embodiment will be explained more specifically below. In this embodiment, calibration data is acquired using a test signal outputted from the test signal generator 15.

When acquiring the calibration data, the operator (radiological technician and medical doctor, etc.) operates buttons provided on an operator console (not shown) whereby a data acquisition start signal is outputted from the operator console to the test signal generator 15 and a switch control apparatus 18. Furthermore, this data acquisition start signal is inputted to the delay time control apparatus 7 and all the calibration data saved in the delay time control apparatus 7 when previous calibration data was acquired is thereby set to zero (or a specific value). The test signal generator 15 generates a test signal through an input of the data acquisition start signal. This test signal is generated asynchronously to a measuring clock of a time counter inputted to the time measuring apparatus 9. Acquiring calibration data requires the test signal to be inputted to each signal processing apparatus 20 connected to a pair of radiation detectors 1. The switch control apparatus 18 starts a corresponding ON, OFF operation of the switch 16 through the input of the data acquisition start signal. That is, the switch control apparatus 18 closes the two switches 16 connected to the two signal processing apparatuses 20 together. Furthermore, the switch control apparatus 18 also closes the switch 21. This switch 21 remains closed during a calibration period. The test signal outputted from the test signal generator 15 is inputted to the pair of signal processing apparatuses 20 through the respective switches 16. When inspecting the examinee, the signal processing apparatus 20 inputs a γ-ray detection signal outputted from the radiation detector 1 and when acquiring calibration data, the signal processing apparatus 20 inputs a test signal through the switch 16.

Here, the opening/closing operation of the switch 16 will be explained. The opening/closing of the switch 16 is controlled by a command signal from the switch control apparatus 18. In this embodiment, in order to acquire calibration data, it is necessary to select a pair of signal processing apparatuses 20; a signal processing apparatus 20 which serves as a reference (hereinafter referred to as "reference signal processing apparatus") and a signal processing apparatus 20 carrying out calibration (hereinafter referred to as "calibration signal processing apparatus") and input a test signal to each signal processing apparatus 20. The test signal is preferably inputted to the pair of signal processing apparatuses 20 simultaneously. Pairs of reference signal processing apparatus 20 and calibration signal processing apparatus 20 are preset and information on many combinations of reference signal processing apparatus 20 and calibration signal processing apparatus 20 that form a pair is stored in a memory (not shown) of the switch control apparatus 18. The reference signal processing apparatus 20 and calibration signal processing apparatus 20 that form a pair correspond to a pair of signal processing apparatuses 20 connected to a pair of radiation detectors 1 located in diametrically opposite directions which detect a pair of γ-rays during an inspection of the examinee. Other combinations of reference signal processing apparatus 20 and calibration signal processing apparatus 20 are also stored in the above described memory. Some reference signal processing apparatuses 20 also serve as calibration signal processing apparatuses 20. The switch control apparatus 18 repeats "close (ON)" and "open (OFF)" operations of the switch 16 connected to a certain reference signal processing apparatus 20 based on the information on the combinations of the reference signal processing apparatus 20 and calibration signal processing apparatus 20 stored in the memory until inputs of test signals to the reference signal processing apparatus 20 and all calibration signal processing apparatuses 20 to be paired therewith are completed. Next, the switch control apparatus 18 sequentially carries out "close" and "open" operations of the calibration signal processing apparatus 20 with respect to the respective switches 16 connected to the reference signal processing apparatus 20. The test signal outputted from the test signal generator 15 is inputted to the calibration signal processing apparatus 20 when the switch 16 is closed and the input of the test signal to the calibration signal processing apparatus 20 is stopped when the switch 16 is opened. That is, the test signal outputted from the test signal generator 15 is inputted to the pairs of reference signal processing apparatus 20 and calibration signal processing apparatus 20 sequentially and reliably. When inputs of a test signal to one reference signal processing apparatus 20 and all calibration signal processing apparatuses 20 to be paired therewith are completed, the switch control apparatus 18 opens the switch 16 connected to the aforementioned reference signal processing apparatus 20 and stops the input of the test signal. Then, the switch control apparatus 18 performs control of turning ON/OFF the respective switches 16 connected to another reference signal processing apparatus 20 and calibration signal processing apparatuses 20 paired therewith until the input of the test signal to all the reference signal processing apparatuses 20 is completed. This is the opening/closing operation of the switch 16.

Next, the method of inputting a test signal to the reference signal processing apparatus 20 and calibration signal processing apparatus 20 and acquiring calibration data using this test signal will be explained more specifically. For convenience, the time measuring apparatus 9 connected to the reference signal processing apparatus 20 will be called a "time measuring apparatus 9A" and the time measuring apparatus 9 connected to the calibration signal processing apparatus 20 will be called a "time measuring apparatus 9B."

The test signal inputted to the reference signal processing apparatus 20 is amplified by the preamplifier 2 and inputted to the timing signal generator 3. The timing signal generator 3 creates a timing signal based on the test signal and outputs the timing signal to the time measuring apparatus 9A. The time measuring apparatus 9A measures the time at which the timing signal arrives and outputs time information (hereinafter referred to as "first time information"). The time measuring apparatus 9B outputs time information (hereinafter referred to as "second time information") based on the timing signal outputted from the timing signal generator 3 of the calibration signal processing apparatus 20 to which the test signal has been inputted. When the pulse height measuring apparatus 12 receives the time information from the time measuring apparatus 9, it obtains a detector ID to identify the radiation detector 1 connected to the time measuring apparatus 9. That is, the pulse height measuring apparatus 12 stores the detector ID corresponding to each time measuring apparatus 9 connected to the pulse height measuring apparatus 12 and when time information is inputted from a certain time measuring apparatus 9, it is possible to identify the detector ID corresponding to the time measuring apparatus 9. This is possible because the time measuring apparatus 9 is provided for each radiation detector 1. When the first time information is inputted to the pulse height measuring apparatus 12, the pulse height measuring apparatus 12 identifies the corresponding detector ID (detector ID of the radiation detector 1 connected to the time measuring apparatus 9A, hereinafter referred to as "first detector ID") and outputs it together with the first time information. The pulse height measuring apparatus 12 identifies the corresponding detector ID (detector ID of the radiation detector 1 connected to the time measuring apparatus 9B, hereinafter referred to as "second detector ID") based on the second time information and outputs it together with the second time information. The coincidence circuit 6 receives the first time information, first detector ID, and second time information and second detector ID outputted from the pulse height measuring apparatus 12. The coincidence circuit 6 calculates a time difference between the first time information which becomes a reference for the pair of radiation detectors 1 and second time information (hereinafter referred to as "arrival time difference"). Even when a test signal is inputted to the same reference signal processing apparatus 20 and calibration signal processing apparatus 20, a variation occurs in the time required for signal transmission, and therefore the test signal is inputted repeatedly to the same pair of signal processing apparatuses 20 and the coincidence circuit 6 calculates the arrival time difference in each case. The delay time control apparatus 7 calculates an average of the arrival time difference obtained from the coincidence circuit 6, calculates the calibration data to be set in all the radiation detectors 1 mounted in the radiation detection apparatus based on the average and causes the calibration data obtained to be stored in the memory of the delay time control apparatus 7. Furthermore, the delay time control apparatus 7 also stores the detector ID corresponding to the calibration data. The test signal is inputted to pairs of opposing signal processing apparatuses 20 until calibration data is created for all signal processing apparatuses 20. The calibration data for each signal processing apparatus 20 and the detector ID corresponding to the calibration data are saved in the delay time control apparatus 7 and this calibration data is used during a PET inspection of the examinee. After the acquisition of calibration data for all the signal processing apparatuses 20 is completed, the switch control apparatus 18 opens the switch 21.

The test signal outputted from the test signal generator 15 is a signal having a sawtooth wave or square wave voltage signal. This test signal is converted to a pulse-shaped charge signal by a capacitor. To obtain time information using the test signal, the amplitude of the waveform may be constant, but by changing the amplitude of the signal waveform, it is possible to calibrate information other than time information, for example, the relationship between the energy of γ-rays and the amplitude of an electric signal outputted from the signal processing apparatus 20.

A CFD (Constant Fraction Discriminator) circuit or leading edge trigger circuit is used for the timing signal generator 3 provided for the signal processing apparatus 20.

This embodiment, which uses a test signal from the test signal generator, can select a reference signal processing apparatus 20 and calibration signal processing apparatus 20 reliably, and can thereby input a test signal to a plurality of reference signal processing apparatuses 20 or a plurality of calibration signal processing apparatuses 20 reliably to acquire calibration data.

Next, the operation of the PET apparatus when carrying out a PET inspection of the examinee will be explained. During a PET inspection, a timing of a γ-ray detection signal is corrected using calibration data obtained using a test signal.

Before starting a PET inspection, PET pharmaceuticals are administered to the examinee by injection, etc., beforehand. The PET pharmaceuticals are selected according to the purpose of the inspection. The PET pharmaceuticals administered to the examinee are concentrated on the affected area of cancer of the examinee. The examinee administered the PET pharmaceuticals are laid on the bed 39.

When starting a PET inspection, the operator operates buttons provided on an operator console (not shown) and outputs an inspection start signal to a centralized control section (not shown). When the inspection start signal is inputted, the centralized control section outputs information on the inspection target range of the examinee and a bed movement start signal to a bed movement control section (not shown). The bed movement control section, which has received the bed movement start signal, moves the bed so that the inspection target range of the examinee enters a γ-ray detection area of the PET apparatus 40 based on the inputted information. The centralized control section, which has received the inspection start signal, transfers the calibration data from the delay time control circuit 7 to the memory (not shown) of the time correction apparatus 10. A PET inspection starts in this state.

Many pairs of γ-rays provoked by the PET pharmaceuticals are emitted in all directions from within the body of the examinee who lays on the bed 39. A pair of γ-rays are emitted in substantially opposite directions and detected by a pair of radiation detectors 1.

When these radiation detectors 1 detect γ-rays, they output pulse-like electric signals (hereinafter referred to as "γ-ray detection signals") according to the energy of γ-rays. Since this γ-ray detection signal is faint, the signal is amplified by the preamplifier 2 and inputted to the timing signal generator 3. The timing signal generator 3 generates a timing signal indicating the time of detection of γ-rays based on the γ-ray detection signal and outputs the timing signal. The time measuring apparatus 9 calculates the arrival time of the timing signal and outputs the time information obtained to the time correction apparatus 10 through the pulse height measuring apparatus 12.

In this embodiment, the time correction apparatus 10 corrects the inputted time information with the calibration data, adjusts the delay in signal transmission and inputs the corrected time information to the coincidence circuit 6. The method of correcting the time information (timing correction method) using the time correction apparatus 10 will be explained below.

Time information corresponding to a γ-ray detection signal of the radiation detector 1 is inputted to the time correction apparatus 10 together with a detector ID which identifies the radiation detector 1. As with the time of acquisition of calibration data, the detector ID is added by the pulse height measuring apparatus 12. The time correction apparatus 10 identifies the radiation detector 1 which outputted the γ-ray detection signal from which the inputted time information derives using the detector ID. The time correction apparatus 10 reads calibration data from the memory based on the detector ID. The time correction apparatus 10 corrects time information based on the calibration data and outputs the corrected time information to the coincidence circuit 6.

When the corrected time information signal is inputted to the coincidence circuit 6, the coincidence circuit 6 decides based on the time information whether the inputted signal is a γ-ray detection signal derived from a pair of γ-rays emitted from the affected area of the examinee provoked by PET pharmaceuticals or not. The coincidence circuit 6 compares time information of two signals out of the time information corresponding to γ-ray detection signals inputted successively and calculates the time difference. The coincidence circuit 6 coincidence-counts γ-ray detection signals corresponding to the calculated time difference which falls within a set time (e.g., 10 nsec) (a pair of γ-ray detection signals produced by annihilation of one positron). The coincidence circuit 6 outputs the detector IDs of the respective radiation detectors which have detected a pair of coincidence-counted γ-rays and information on the coincidence count to the data collection apparatus 31.

The information inputted to the data collection apparatus 31 is saved in the data saving apparatus 32 and after all measurements are completed, data is outputted to the image reconstruction apparatus 33. The image reconstruction apparatus 33 creates information on the tomogram including the affected area of the examinee based on the information. The tomographic image is displayed on the display device 34.

This embodiment is intended to correct the difference in the transmission time of γ-ray detection signals between detector channels (including the signal processing apparatuses 20) using the calibration data obtained using the aforementioned test signal.

This embodiment allows the following effects to be obtained.

(1) In this embodiment, a test signal outputted from the test signal generator 15 is inputted to the signal processing apparatus 20, and therefore it is possible to input a test signal to all the signal processing apparatuses 20 reliably and acquire calibration data of timings corresponding to detection signals of all the radiation detectors included in the PET apparatus 40 in a short time. Especially, this embodiment inputs a test signal to the preamplifier 2, and therefore it is possible to obtain more accurate calibration data which reflects propagation times of a signal at the preamplifier 2 and timing signal generator 3. It is also possible to obtain calibration data in a shorter time than the conventional example by connecting the test signal generator 15 between the preamplifier 2 and timing signal generator 3 and inputting a test signal, which is an electric signal, to the timing signal generator 3. However, in this case, the accuracy of calibration data is reduced compared to the case where a test signal is inputted to the preamplifier 2 because the time for signal transmission at the preamplifier 2 cannot be reflected. When a test signal is selectively inputted to the respective radiation detectors 1 using the test signal generator 15, it is necessary to use radiation or a very short light pulse signal as the test signal. However, it is difficult to realize the input of such a test signal to the radiation detector 1. Therefore, it is desirable to input the test signal to the signal processing apparatus 20 without passing through the radiation detector 1.

(2) In this embodiment, the electric signal used as a test signal is easier to handle than a radiation source used in the conventional example.

(3) In this embodiment, when calibration data is acquired, the switch control apparatus 18 turns ON/OFF many switches 16 sequentially to input a test signal to the corresponding pair of signal processing apparatuses 20, and therefore it is possible to input the test signal to all the signal processing apparatuses 20 reliably. Furthermore, compared to a case where the signal processing apparatus 20 is selected manually, it is possible to drastically reduce time and trouble.

In this embodiment, a test signal is inputted to a pair of signal processing apparatuses 20 respectively, but the number of signal processing apparatuses 20 to which a test signal is inputted is not always 2 and it is possible to input a test signal to three or more signal processing apparatuses 20 to acquire calibration data. That is, the switch control apparatus 18 turns ON, three or more, for example, ten switches 16 connected to ten signal processing apparatuses 20. A test signal from the test signal generator 15 is inputted to the ten corresponding signal processing apparatuses 20. The coincidence circuit 6 calculates an arrival time difference for each combination of two out of ten signal processing apparatuses 20. Information on combinations of signal processing apparatuses 20 for which an arrival time difference is calculated is preset and stored in a memory (not shown) of the coincidence circuit 6. Thus, by inputting a test signal to three or more signal processing apparatuses 20 simultaneously, it is possible to further shorten the time required to acquire calibration data corresponding to all radiation detectors 1.

(4) This embodiment outputs a test signal outputted from the test signal generator 15 asynchronously to the clock for measuring an arrival time. Such asynchronous outputting eliminates any correlation between a pseudo-signal generation system and coincidence count system, and can thereby perform accurate calibration.

(5) This embodiment converts a signal detected by the radiation detector 1 and a test signal from the test signal generator to digital values and processes the digitized time data. Using such a digital calculation facilitates the setting of a time window. Furthermore, the digital circuit can be integrated more easily than a digital/analog circuit.

Embodiment 2

Figure 3:
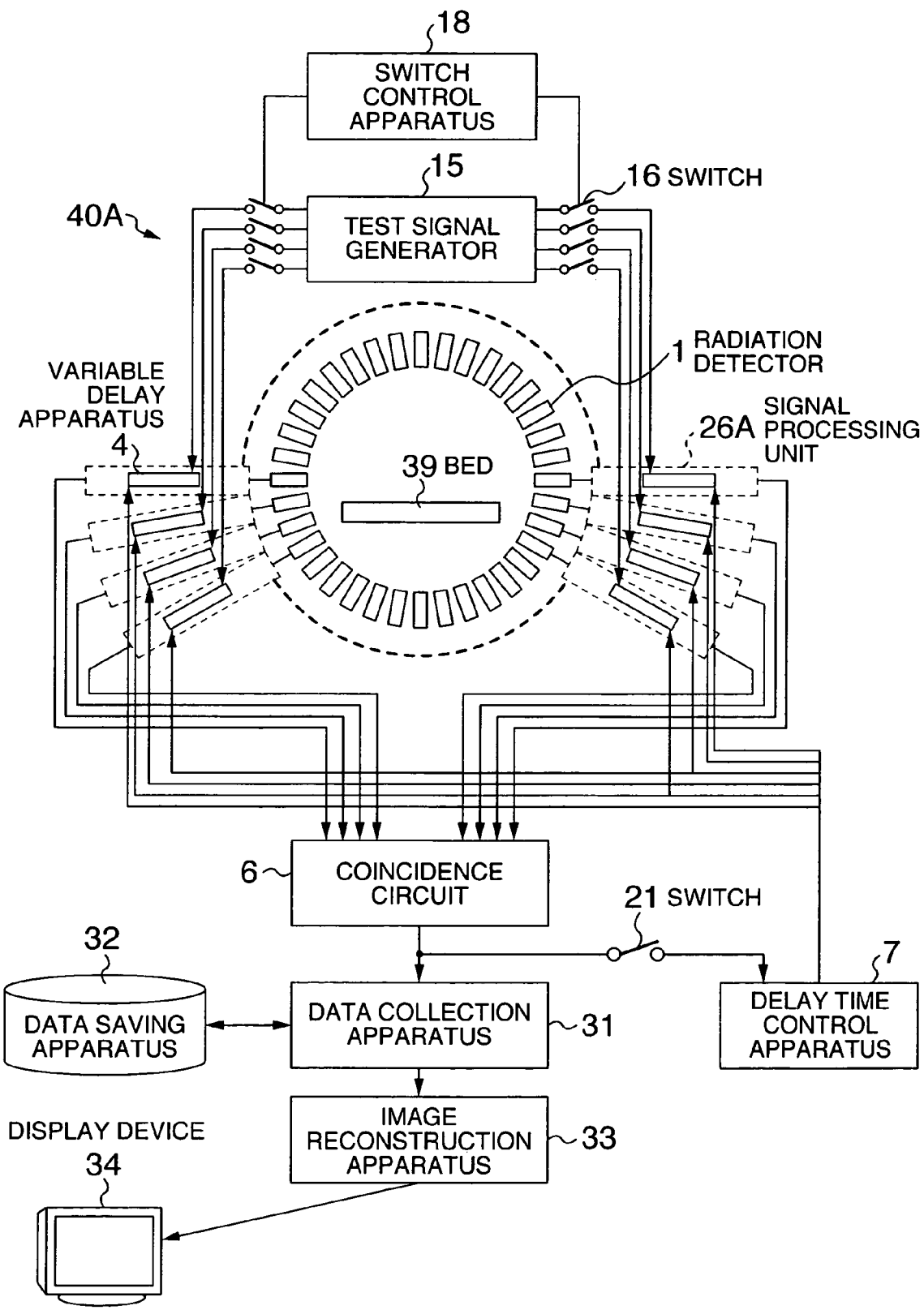
FIG. 3 is a block diagram of a PET apparatus which is another embodiment of the present invention.
Figure 4:
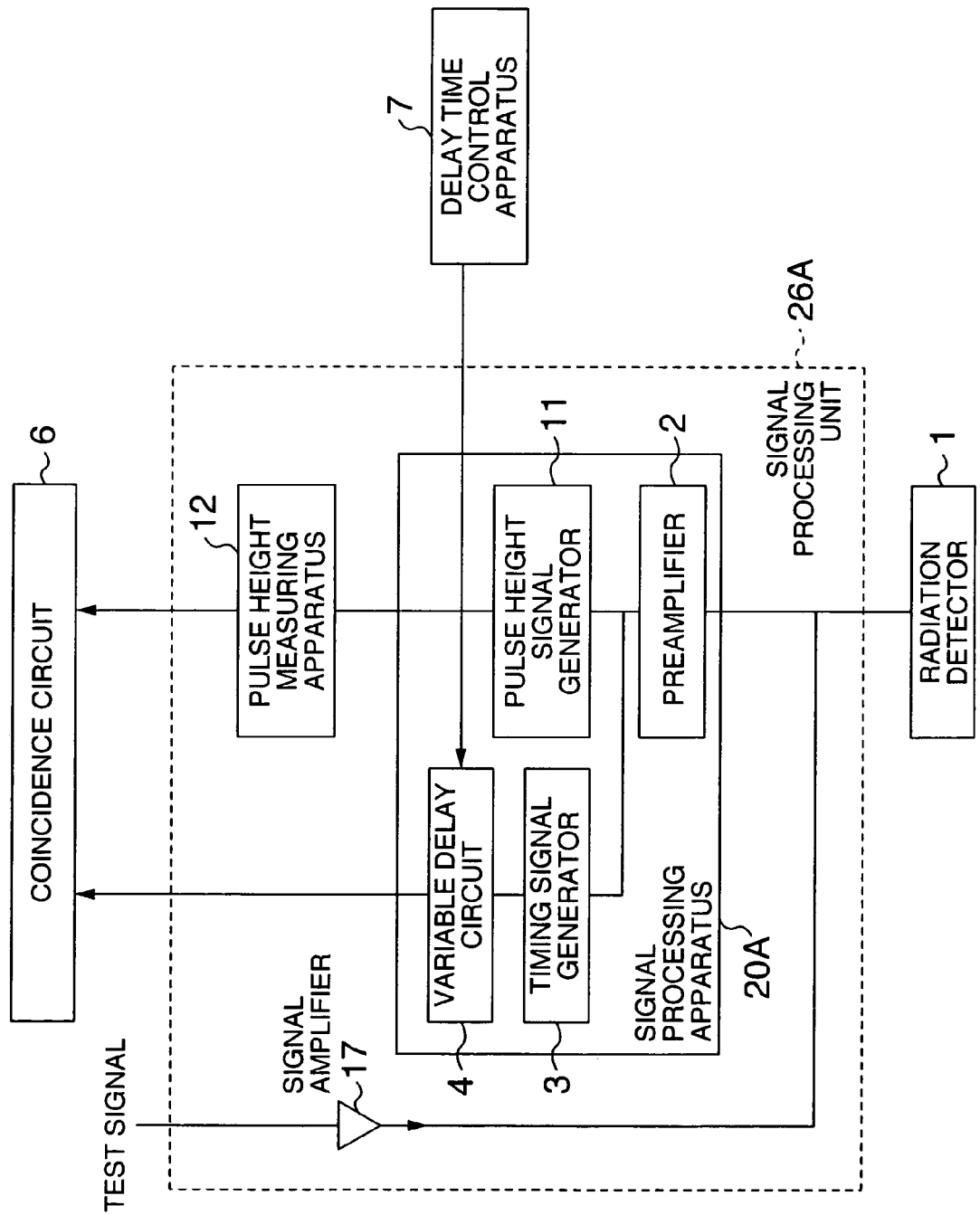
FIG. 4 is a detailed block diagram of the signal processing unit shown in FIG. 3.

A radiological imaging apparatus which is another embodiment of the present invention will be explained using FIG. 3 and FIG. 4 below. The radiological imaging apparatus of this embodiment is a PET apparatus.

The PET apparatus 40A of this embodiment has a configuration with the time correction apparatus 10 in the PET apparatus 40 of Embodiment 1 replaced by a variable delay circuit (delay adjustment apparatus) 4. The PET apparatus 40A provides a signal processing unit 26A for each radiation detector 1. The signal processing unit 26A is provided with a signal processing apparatus 20A which is the signal processing apparatus 20 provided with the variable delay circuit 4. The variable delay circuit 4 has its input end connected to a timing signal generator 3 and its output end connected to a coincidence circuit 6. A pulse height measuring apparatus 12 is connected to a pulse height signal generator 11 and the coincidence circuit 6. The rest of the structure of the PET apparatus 40A is the same as that of the PET apparatus 40.

When calibration data is acquired, a data acquisition start signal is inputted to a test signal generator 15 and a switch control apparatus 18 as in the case of Embodiment 1. The switch control apparatus 18 closes a pair of switches 16 connected to the corresponding pair of reference signal processing apparatus 20 and calibration signal processing apparatus 20. A test signal outputted from the test signal generator 15 is inputted to the reference signal processing apparatus 20 and calibration signal processing apparatus 20 through the respective switches 16.

The opening/closing operation of the switch 16 is the same as that of Embodiment 1, and therefore explanations thereof will be omitted.

A test signal inputted to the respective signal processing apparatuses 20 is amplified by a preamplifier 2 and then inputted to the timing signal generator 3. The timing signal generator 3 generates a timing signal based on the test signal and outputs the timing signal to a variable delay circuit 4. When calibration data is acquired, a delay time control apparatus 7 sets an amount of delay of the variable delay circuit 4 (hereinafter referred to as "reference variable delay circuit 4A") connected to the reference signal processing apparatus 20 to a constant value (e.g., a median value within the variable range). Furthermore, the amount of delay of the variable delay circuit 4 (hereinafter referred to as "calibration variable delay circuit 4B") connected to the calibration signal processing apparatus 20 is set to a minimum value. The variable delay circuit 4 delays and outputs the timing signal based on the set amount of delay. The pulse height measuring apparatus 12 calculates a pulse height based on the pulse height signal outputted from the pulse height signal generator 11 and identifies the corresponding detector ID. The coincidence circuit 6 calculates sensitivity based on the delayed timing signal and pulse height information. When the amount of delay set in the calibration variable delay circuit 4B is changed, the sensitivity to be calculated by the coincidence circuit 6 also changes. The amount of delay time set in the calibration variable delay circuit 4B is gradually increased from the initially set value and the amount of delay time corresponding to the maximum sensitivity is calculated. The information of the amount of delay corresponding to the maximum sensitivity is transmitted to the delay time control apparatus 7 and stored in a memory (not shown) of the delay time control apparatus 7. In this way, it is possible to obtain calibration data corresponding to all signal processing apparatuses 20, and the calibration data and the corresponding detector IDs are stored in the memory of the delay time control apparatus 7.

The operation of the PET apparatus during a PET inspection of the examinee will be explained using FIG. 3.

Differences from Embodiment 1 will be explained. When an inspection start signal is inputted to an overall control section (not shown), the overall control section sends a delay amount setting signal to the delay time control apparatus 7. The delay time control apparatus 7 which has received the delay amount setting signal sends a command signal to the corresponding variable delay circuit 4 so as to set the amount of delay (calibration data) to be set based on the detector ID (stored in the memory) of the radiation detector 1 connected to the variable delay circuit 4. That is, before a PET inspection, the delay time control apparatus 7 sets an amount of delay in all the variable delay circuits 4 to obtain maximum sensitivity based on the calibration data saved in the memory. Furthermore, during a PET inspection, a switch 21 set between the coincidence circuit 6 and the delay time control apparatus 7 is opened so that no γ-ray detection signal is inputted to the delay time control apparatus 7.

A pair of γ-rays emitted from within the body of the examinee lying on the bed 39 by being provoked by PET pharmaceuticals are detected by a pair of radiation detectors 1. Based on the γ-ray detection signals outputted from the radiation detectors 1, the timing signal generated by the timing signal generator 3 is inputted to the coincidence circuit 6 through the corresponding variable delay circuit 4. That is, the variable delay circuit 4 outputs the timing signal (time information) corrected based on the set amount of delay to the coincidence circuit 6. The coincidence circuit 6 carries out coincidence counting similar to that in Embodiment 1 based on the timing signal. The coincidence circuit 6 outputs detector IDs of the respective radiation detectors which have detected a pair of coincidence-counted γ-rays and information on the coincidence count value to a data collection apparatus 31.

The signal inputted to the data collection apparatus 31 is saved in a data saving apparatus 32 and data is outputted to an image reconstruction apparatus 33 after all measurements are completed. An image of the affected area of the examinee is created based on the data processed by the image reconstruction apparatus 33 and the image is displayed on a display device 34.

A time window of the coincidence circuit 6 set when acquiring calibration data of the PET apparatus 40A is preferably wider than during a PET inspection. Before calibration data is acquired, even if a test signal is inputted to the reference signal processing apparatus 20 and calibration signal processing apparatus 20 simultaneously, the signal arrives at the coincidence circuit 6 with a time variation. When the time window of the coincidence circuit 6 is narrow, even the test signals which have been inputted simultaneously may be processed as non-coincidence signals by the coincidence circuit 6. For that reason, it is preferable to set a wide time window for the coincidence circuit 6 when calibration data is acquired. In addition to the widening of the set value of the time window, it is possible to prevent a test signal from being processed as a non-coincidence signal by setting a time period after a test signal is inputted to the calibration signal processing apparatus 20 until a test signal is inputted to the next calibration signal processing apparatus 20 to a value greater than a certain value.

This embodiment also inputs a test signal (electric signal) outputted from the test signal generator 15 to the signal processing apparatus 20, and therefore it is possible to obtain the effects (1), (2) produced in Embodiment 1.

Embodiment 3

Figure 5:
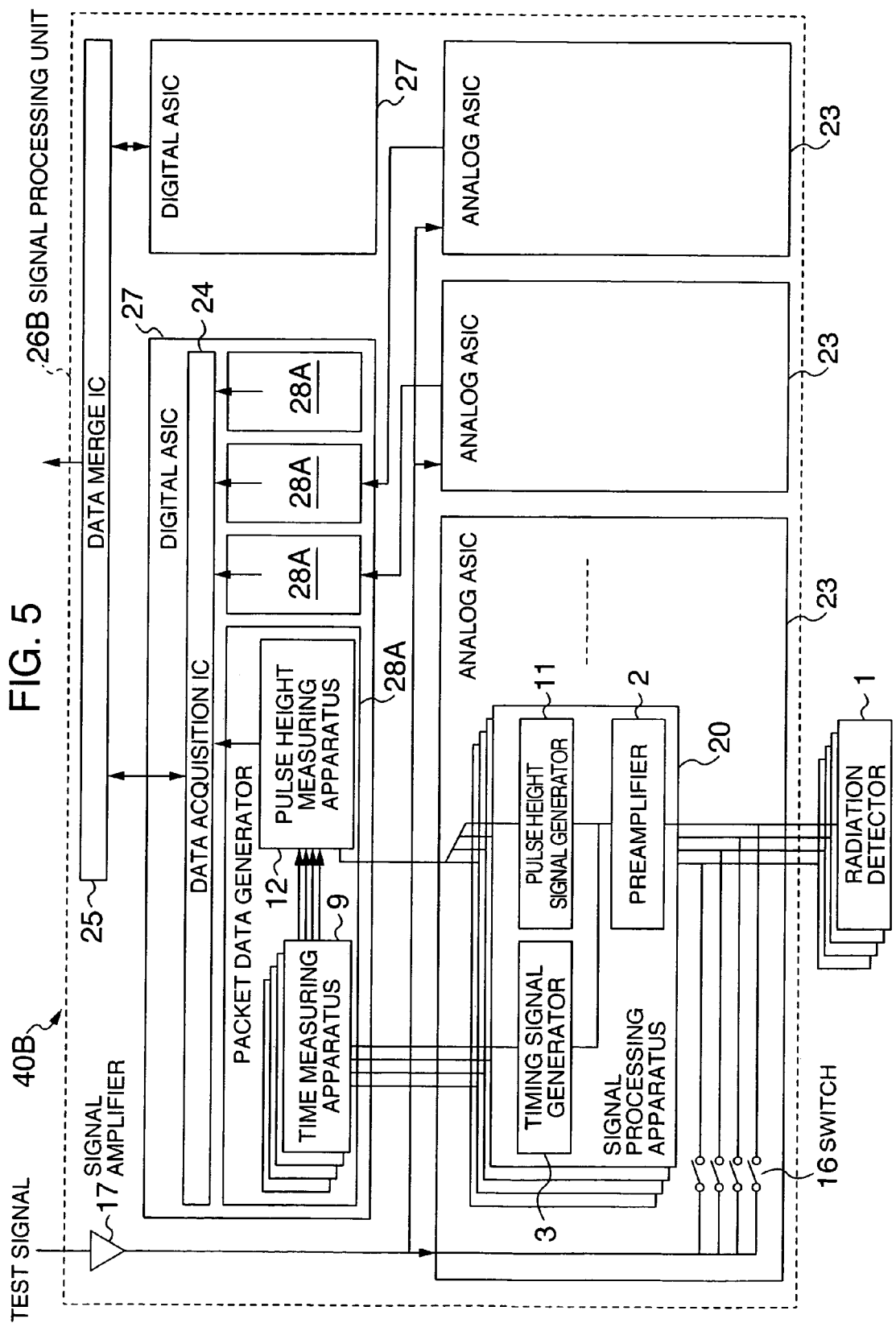
FIG. 5 is block diagram of a signal processing unit of a PET apparatus which is a further embodiment of the present invention.

A radiological imaging apparatus which is a further embodiment of the present invention will be explained using FIG. 5. The radiological imaging apparatus of this embodiment is a PET apparatus 40B and different from the PET apparatus 40 in Embodiment 1 in that a plurality of signal processing units 26B are provided. The structure of the PET apparatus 40B other than the signal processing unit 26B is the same as that of the PET apparatus 40.

The signal processing unit 26B is provided with a signal amplifier 17, a plurality of analog ASICs 23, a plurality of digital ASICs 27 and a data merge IC 25. Several tens of signal processing units 26B are arranged in the PET apparatus 40B. 90 analog ASICs 23 are arranged for one signal processing unit 26B. Furthermore, a CFD (Constant Fraction Discriminator) circuit or leading edge trigger circuit is used for the timing signal generator 3. The signal amplifier 17 is connected to a test signal generator 15. The analog ASIC 23 is provided with a plurality of signal processing apparatuses 20 and the same number of switches 16. Each signal processing apparatus 20 is provided with a preamplifier 2, and a timing signal generator 3 and a pulse height signal generator 11 connected to the preamplifier 2. The preamplifier 2 is connected to a radiation detector 1. Each switch 16 provided for the analog ASIC 23 is connected to the preamplifier 2 of each signal processing apparatus 20. These switches 16 are connected to the signal amplifier 17. In this embodiment, the signal amplifier 17 is connected to the respective switches 16 of all the analog ASICs 23 provided within the signal processing unit 26B. The digital ASIC 27 includes a plurality of packet data generators 28A and a data acquisition IC 24. The packet data generator 28A is connected to each analog ASIC 23 and provided with a time measuring apparatus 9 which is individually connected to each timing signal generator 3 of one analog ASIC 23. The respective time measuring apparatuses 9 of the packet data generator 28A are connected to one pulse height measuring apparatus 12. The pulse height measuring apparatus 12 is connected to each pulse height signal generator 11 of one corresponding analog ASIC 23. The pulse height measuring apparatus 12 of each packet data generator 28A is connected to the data acquisition IC 24. The data integration IC 25 connected to a coincidence circuit 6 is connected to the pulse height signal generator 11 of each packet data generator 28A.

The pulse height measuring apparatus 12 receives time information on the time at which γ-rays are detected from the time measuring apparatus 9 and identifies the detector ID. Furthermore, the pulse height measuring apparatus 12 measures pulse height information of a γ-ray detection signal proportional to the energy of γ-rays based on the output from the pulse height signal generator 11 connected to the pulse height measuring apparatus 12. The pulse height measuring apparatus 12 also functions as an information integration apparatus that integrates time information, detector ID information (detector position information) and pulse height information. The information integration apparatus outputs the integrated information (packet information) which is digital information including those three types of information to the data acquisition IC 24. The packet data (including time information, detector ID and pulse height information) outputted from the pulse height measuring apparatus 12 of each packet data generator 28A is outputted to the coincidence circuit 6 (see FIG. 1) in the following stage through the data merge IC 25.

This embodiment can obtain the effects (1) to (5) produced in Embodiment 1 and can also obtain the following effects.

(6) Since this embodiment sets each switch 16 in the analog ASIC 23, wiring which transmits a test signal to the respective switches 16 can be shared. For this reason, it is possible to drastically reduce the number of wires connecting the test signal generator 15 and the respective switches 16. Therefore, when the test signal generator 15 is provided and wiring of the PET apparatus 40B is carried out, it is possible to simplify the wiring work. The switches 16 are connected to the respective signal processing apparatuses 20 included in the analog ASIC 23, but it is also possible to achieve the same effect even if the switches 16 are set between the signal processing apparatus 20 and time measuring apparatus 9.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A positron emission tomography, comprising:
    a plurality of radiation detectors arranged around a bed supporting an object to be inspected;
    a plurality of signal processing apparatuses each connected to each of said plurality of radiation detectors;
    a test signal generator for outputting test signals to a plurality of said signal processing apparatuses;
    a plurality of gate apparatuses for transferring said test signals, said gate apparatuses connected to said test signal generator and individually connected to a plurality of said signal processing apparatuses;
    a controller for controlling open and close of a pair of said gate apparatuses on the basis of combination information of a pair of said signal processing apparatuses, said gate apparatuses paired being connected to said signal processing apparatuses paired respectively, one of said signal processing apparatuses paired being previously set as a reference and the other being previously set as a signal processing apparatus to be calibrated;

a calibration data generator for generating timing calibration data for each of said signal processing apparatuses on the basis of outputs of said signal processing apparatuses paired, said outputs generated based on said test signals each input to each of said signal processing apparatuses paired; and timing correction means for correcting timings of radiation detection signals output from said radiation detectors on the basis of said timing calibration data.

2. A positron emission tomography according to claim 1, wherein a plurality of said gate apparatuses are connected to said test signal generator using shared wiring.

3. A positron emission tomography according to claim 1, further comprising a coincidence apparatus to which an output of said timing correction means is input.

4. A positron emission tomography, comprising:
a plurality of radiation detectors arranged around a bed supporting an object to be inspected;
a plurality of signal processing apparatuses each connected to each of a plurality of said radiation detectors;
a test signal generator for outputting test signals to a plurality of said signal processing apparatuses;
a plurality of gate apparatuses for transferring said test signals, said gate apparatuses connected to said test signal generator and separately connected to a plurality of said signal processing apparatuses;
a controller for controlling open and close of a pair of said gate apparatuses on the basis of combination information of a pair of said signal processing apparatuses, said gate apparatuses paired being connected to said signal processing apparatuses paired respectively, one of said signal processing apparatuses paired being previously set as a reference and the other being previously set as a signal processing apparatus to be calibrated;
a plurality of time generators each connected to each of a plurality of said signal processing apparatuses, each of said time generators generating time information on the basis of an output of a corresponding one of said signal processing apparatuses;
a calibration data generator for generating timing calibration data for each of a plurality of said signal processing apparatuses on the basis of outputs of said signal processing apparatuses paired, said outputs generated based on said test signals each input to each of said signal processing apparatuses paired; and
a time correction apparatus connected to a plurality of said time generators for correcting said time information output from said time generators on the basis of said timing calibration data.

5. A positron emission tomography according to claim 4, further comprising a coincidence apparatus to which time information corrected by said time correction apparatus is input.

6. A positron emission tomography according to claim 4, wherein a plurality of said gate apparatuses are connected to said test signal generator using shared wiring.

7. A positron emission tomography, comprising:
a plurality of radiation detectors arranged around a bed supporting an object to be inspected;
a plurality of signal processing apparatuses each connected to each of said plurality of radiation detectors;
a test signal generator for outputting test signals to a plurality of said signal processing apparatuses;
a plurality of gate apparatuses for transferring said test signals, said gate apparatuses connected to said test signal generator and individually connected to a plurality of said signal processing apparatuses;
a controller for controlling open and close of a pair of said gate apparatuses on the basis of combination information of a pair of said signal processing apparatuses, said gate apparatuses paired being connected to said signal processing apparatuses paired respectively, one of said signal processing apparatuses paired being previously set as a reference and the other being previously set as a signal processing apparatus to be calibrated;
a delay adjustment apparatus connected to a plurality of said signal processing apparatuses individually, for adjusting amounts of delay of outputs of said signal processing apparatuses;
a calibration data generator for generating timing calibration data on the basis of outputs of said signal processing apparatuses paired, said outputs generated based on said test signals each input to each of said signal processing apparatuses paired and for adjusting an amount of delay of said delay adjustment apparatus on the basis of said timing calibration data.

8. A positron emission tomography according to claim 7, further comprising a coincidence apparatus to which an output of said delay adjustment apparatus is input.

9. A positron emission tomography according to claim 7, wherein a plurality of said gate apparatuses are connected to said test signal generator using shared wiring.

10. A method of correcting a timing in a positron emission tomography, comprising the steps of:
previously setting a combination of a pair of signal processing apparatuses, one of which is a signal processing apparatus as a reference and the other of which is a signal processing apparatus to be calibrated;
inputting test signals generated from a test signal generator to said signal processing apparatuses paired respectively, via a pair of gate apparatuses closed by a controller, said signal processing apparatuses paired being connected to a pair of radiation detectors and said gate apparatuses paired;
generating a timing calibration data on the basis of each output of said signal processing apparatuses paired, said each output generated based on said test signals; and
correcting timings of radiation detection signals output from said radiation detectors on the basis of said timing calibration data.

11. A method of correcting a timing in a positron emission tomography according to claim 10, wherein said test signals are electric signals.

12. A method of correcting a timing in a positron emission tomography according to claim 11, wherein said test signals are input to selected ones of a plurality of said signal processing apparatuses.

13. A method of correcting a timing in a positron emission tomography according to claim 10, wherein said test signals are input to selected ones of a plurality of said signal processing apparatuses.

14. A method of correcting a timing in a positron emission tomography according to claim 13, wherein said test signals are input to said signal processing apparatuses connected to said radiation detectors without passing through said radiation detectors.

15. A method of correcting a timing in a positron emission tomography according to claim 10, wherein said test signals are input to said signal processing apparatuses connected to said radiation detectors without passing through said radiation detectors.

16. A method of correcting a timing in a positron emission tomography according to claim 15, wherein said test signals are input to two or more of said signal processing apparatuses.

17. A method of correcting a timing in a positron emission tomography according to claim 10, wherein said test signals are input to two or more of said signal processing apparatuses.

18. A method of correcting a timing in a positron emission tomography according to claim 17, wherein said step of generating a timing calibration data comprising the steps of:
generating time information by a time generator on the basis of outputs of said signal processing apparatuses to which said test signals are input; and
generating calibration data on the basis of said time information,
wherein said test signals are asynchronously output with respect to measurement clocks input to said time generator for generation of said time information.

19. A method of correcting a timing in a positron emission tomography according to claim 10, wherein said step of generating a timing calibration data comprising the steps of:
generating time information by a time generator on the basis of outputs of said signal processing apparatuses to which said test signals are input; and
generating calibration data on the basis of said time information,
wherein said test signals are asynchronously output with respect to measurement clocks input to said time generator for generation of said time information.

* * * * *